| United States Patent [19] | [11] Patent Number: 4,905,268 |
|---|---|
| Mattson et al. | [45] Date of Patent: Feb. 27, 1990 |

[54] ADJUSTABLE OFF-FOCAL APERTURE FOR X-RAY TUBES

[75] Inventors: Rodney A. Mattson, Mentor; Robert E. Levar, Willoughby, both of Ohio

[73] Assignee: Picker International, Inc., Highland Hts., Ohio

[21] Appl. No.: 222,521

[22] Filed: Jul. 21, 1988

Related U.S. Application Data

[63] Continuation of Ser. No. 46,860, May 7, 1987, which is a continuation-in-part of Ser. No. 791,210, Oct. 25, 1985, Pat. No. 4,672,648.

[51] Int. Cl.⁴ ............................ G21K 3/00; G21K 1/04
[52] U.S. Cl. .................................... 378/158; 378/200; 378/150; 378/156
[58] Field of Search ..................... 378/7, 153, 150, 160, 378/4, 19, 146, 147, 148, 202, 200, 203, 156, 158

[56] References Cited

U.S. PATENT DOCUMENTS

| 1,164,987 | 12/1915 | Bucky . | |
|---|---|---|---|
| 1,738,945 | 12/1929 | Breukert et al. . | |
| 1,909,118 | 5/1933 | Raab . | |
| 2,216,326 | 10/1940 | Smith | 250/63 |
| 2,638,554 | 5/1953 | Bartow et al. | 250/99 |
| 3,023,317 | 2/1962 | Hura | 250/105 |
| 3,448,270 | 6/1969 | Peyser | 250/105 |
| 3,631,249 | 12/1971 | Friede . | |
| 3,699,379 | 9/1971 | Peyser | 250/105 |
| 3,755,672 | 8/1973 | Edholm et al. | 250/322 |
| 3,829,701 | 8/1974 | Hura | 250/511 |
| 3,849,649 | 11/1974 | Carey | 378/153 |
| 3,921,000 | 11/1975 | Muehllehner | 250/505 |
| 3,937,963 | 2/1976 | Hounsfield | 250/363 |
| 4,096,391 | 6/1978 | Barnes | 250/505 |
| 4,101,768 | 7/1978 | Lill | 250/360 |
| 4,107,562 | 8/1978 | Koller et al. | 378/200 |
| 4,181,858 | 1/1980 | Moore | 250/445 |
| 4,195,229 | 3/1980 | Suzuki . | |
| 4,219,734 | 8/1980 | Chery . | |
| 4,221,971 | 9/1980 | Burger | 378/148 |
| 4,255,664 | 3/1981 | Rutt et al. | 250/445 |
| 4,277,684 | 7/1981 | Carson | 250/445 |
| 4,277,685 | 7/1981 | Covic et al. | 378/007 |
| 4,304,999 | 12/1981 | Richey et al. | 250/445 |
| 4,347,440 | 8/1982 | Haas | 378/156 |
| 4,369,517 | 1/1983 | Ozawa | 378/200 |

FOREIGN PATENT DOCUMENTS

| 1147069 | 5/1983 | Canada | 358/27 |
|---|---|---|---|
| 628479 | 6/1931 | Fed. Rep. of Germany . | |
| 913678 | 6/1954 | Fed. Rep. of Germany . | |
| 2619008 | 11/1977 | Fed. Rep. of Germany . | |
| 2038757 | 12/1970 | France . | |
| 2400717 | 8/1978 | France . | |
| 2398487 | 2/1979 | France . | |
| 7730533 | 4/1979 | France . | |
| 2004448 | 8/1977 | United Kingdom . | |

OTHER PUBLICATIONS

European Search Report PCT/GB 86/00655, Jan. 16, 1987.

Primary Examiner—Janice A. Howell
Assistant Examiner—Joseph A. Hynds
Attorney, Agent, or Firm—Fay, Sharpe, Beall, Fagan, Minnich & McKee

[57] ABSTRACT

A radiographic apparatus (10) includes an x-ray tube (16), an off-focal radiation collimator (20), a shutter (22), and a primary beam defining collimator (24) between the x-ray tube and patient receiving region (14). The off-focal collimator is mounted within a collar (48) which surrounds an x-ray port (36) of the x-ray tube. The tube port is sealed from the atmosphere by an aluminum window (46). A plate (62) of a radiation blocking material is rotatably mounted by a bearing (70) within the collar closely adjacent the aluminum window. By rotating the moveable plate, aperture or radiation passing slots or portions (62, 64) of different sizes are selectively brought into alignment between a focal spot (34) of the x-ray tube and a radiation passing region or slot (52) of a stationary plate (50) at the distal end of the collar. The aligned slots block the passage of off-focal radiation. Moreover, rotating slots of different sizes into alignment changes the size or angle of the x-ray fan beam.

13 Claims, 3 Drawing Sheets

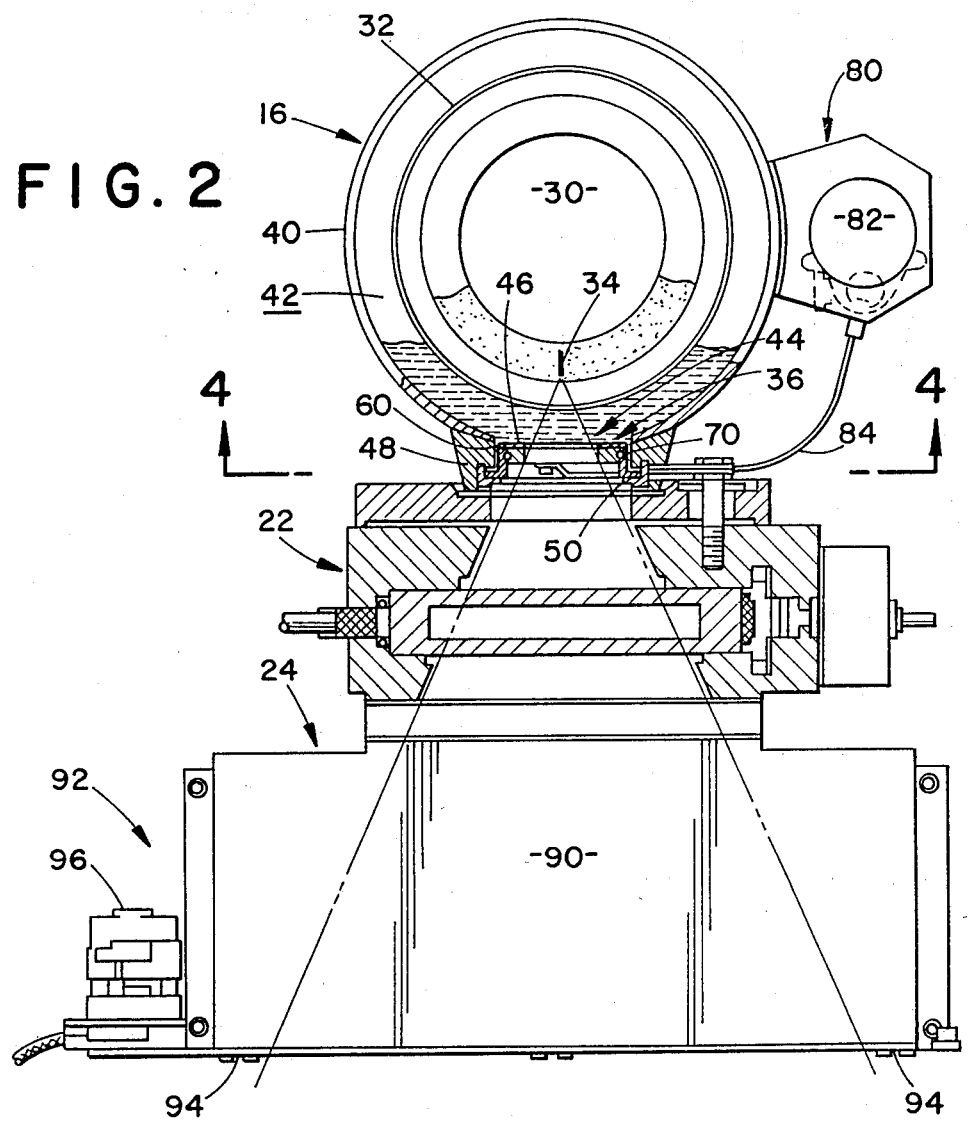
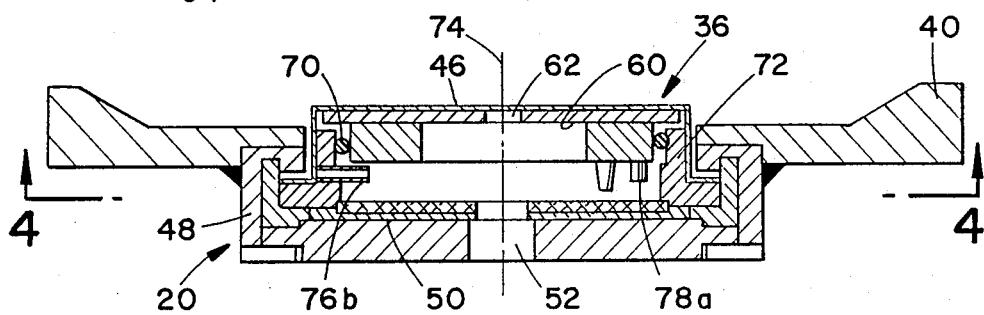

ADJUSTABLE OFF-FOCAL APERTURE FOR X-RAY TUBES

This application is continuation of U.S. application Ser. No. 046,860, filed May 7, 1987 which is a continuation-in-part of U.S. application Ser. No. 791,210, filed Oct. 25, 1985, entitled "Improved Apparatus and Method for Radiation Attenuation", now U.S. Pat. No. 4,672,648.

BACKGROUND OF THE INVENTION

The present invention relates to the field of radiography. It finds particular application in conjunction with the x-ray tubes for computed tomographic scanners and will be described with particular reference thereto. However, it is to be appreciated that the invention may find further application in other areas of radiography, such as medical diagnostic digital x-ray, conventional x-ray, radiation therapy, and the like.

In computed tomography, a slice of a patient to be examined is disposed in a scan circle of the scanner. A fan shaped x-ray beam is projected from an x-ray tube through a shutter, a collimator, the scan circle, and the patient slice to an array of radiation detectors. By rotating the radiation source, shutter, and collimator relative to the patient, radiation is projected through the imaged slice to the detectors from a multiplicity of directions. From radiation intensity data sampled at the detectors, data indicative of the path the sampled radiation traveled to reach each sampled detector, and other data, an image of the examined slice of the patient is reconstructed.

One of the problems encountered in CT scanners is the deleterious effect of off-focal radiation. In the x-ray tube, an electron beam strikes a focal spot point or line on an anode. X-rays are generated at this focal spot and travel along diverging linear paths in an x-ray fan beam of dimension controlled by the collimator. If all the radiation were emitted from the focal spot, then the path traveled by each x-ray beam from the x-ray tube to the detector for each detector sampling could be accurately determined. However, x-rays are emitted from regions of the anode other than the focal spot. In CT scanning x-ray tubes, 3% to 8% of the detected radiation is commonly off-focal radiation, i.e. radiation not originating at the focal spot. The spread in the origin of the radiation from off-focal radiation causes small objects and sharp edges to lose proper definition and become blurred. The lack of definition gives rise to non-linear artifacts in the reconstructed image.

The CT scanner collimators are commonly disposed adjacent the scan circle, i.e. displaced from the x-ray tube anode. Although this placement assures accurate beam dimensions in the scan circle, off-focal radiation originating on portions of the anode well displaced from the focal spot are permitted to pass through the collimator to the detectors. The greater the distance between the anode and the collimator, the greater the parallax and off-focal radiation may originate more distantly from the focal spot and still pass through the collimator to the detectors, i.e. the more blurred the focal spot becomes.

The off-focal radiation has a particularly deleterious effect on the bone correction applied to brain scans. A calcium correction is commonly made to minimize the effects attributable to radiation spectrum changes due to absorption by the bone tissue. The calcium correction deconvolves the effect of the broad spectrum radiation source's projection across the bone/brain interface on the soft tissue. The variety of sizes, shapes, and density of skulls which may be examined in common clinical practice render impractical a universal correction for the effects of off-focal radiation and beam hardening.

The present invention includes a method and apparatus for reducing off-focal radiation for head scans without affecting whole body scans.

SUMMARY OF THE INVENTION

In accordance with one aspect of the present invention, an x-ray tube assembly for CT scanners is provided. An anode is rotatbly mounted within an evacuated envelope. A housing surrounds the envelope to define a cooling fluid receiving reservoir. An x-ray port is defined by an x-ray permeable, fluid impermeable window which seals an aperture through the housing. An x-ray beam defining means includes a first radiation stopping plate with a first beam defining aperture therein. The first radiation stopping plate is mounted to a collar which surrounds the window. A second radiation stopping plate which defines first and second aperture portions therethrough is moveably mounted to the collar to be moveable at least between a first position in which the first aperture portion is aligned with the first beam defining aperture and a second position in which the second aperture portion is aligned with the first beam defining aperture. Preferably, the first aperture portion is a slot of relatively short width to attenuate off-focal radiation during a head scan and the second aperture portion is a longer slot of sufficient length that the x-ray beam is not obstructed during a body scan. Means are provided for moving the second radiation stopping plate at least between the first and second positions.

In accordance with a more limited aspect of the present invention, the second radiation stopping plate is rotatably mounted adjacent an inner most end of the x-ray tube collar. This positions the second plate in the closest proximity to the x-ray tube anode.

In accordance with another more limited aspect of the present invention, the x-ray tube assembly is combined with a CT scanner, which scanner includes an x-ray beam shutter and an x-ray beam collimator.

One advantage of the present invention is that it reduces off-focal radiation, particularly during head scans.

Another advantage of the present invention is that it is disposed within the confines of a conventional x-ray tube assembly. This simplifies and facilitates installation, particularly the retrofitting of scanners already in place.

Yet another advantage of the present invention is that it selectively adjusts the fan angle or other dimensions of a beam of x-rays to accommodate the examination of regions of different sizes.

Still further advantages of the present invention will become apparent to those of ordinary skill in the art upon reading and understanding the following detailed description of the preferred embodiment.

BRIEF DESCRIPTION OF THE DRAWINGS

The invention may take form in various steps and arrangements of steps or in various components and arrangements of components. The drawings are only for purposes of illustrating a preferred embodiment and are not to be construed as limiting the invention.

FIG. 2 is a side view in partial section of an x-ray tube assembly including an adjustable off-focal radiation controller, a shutter, and a collimator assembly;

FIG. 3 is an enlarged view of an x-ray exit port of the x-ray tube of FIG. 2 including the adjustable off-focal radiation collimator;

FIG. 4 is a sectional view through section 4—4 of FIG. 2; and,

FIG. 5 is a bottom view of the collimator assembly of FIG. 2.

DETAILED DESCRIPTION OF THE PREFERRED EMBODIMENTS

Figure 1:
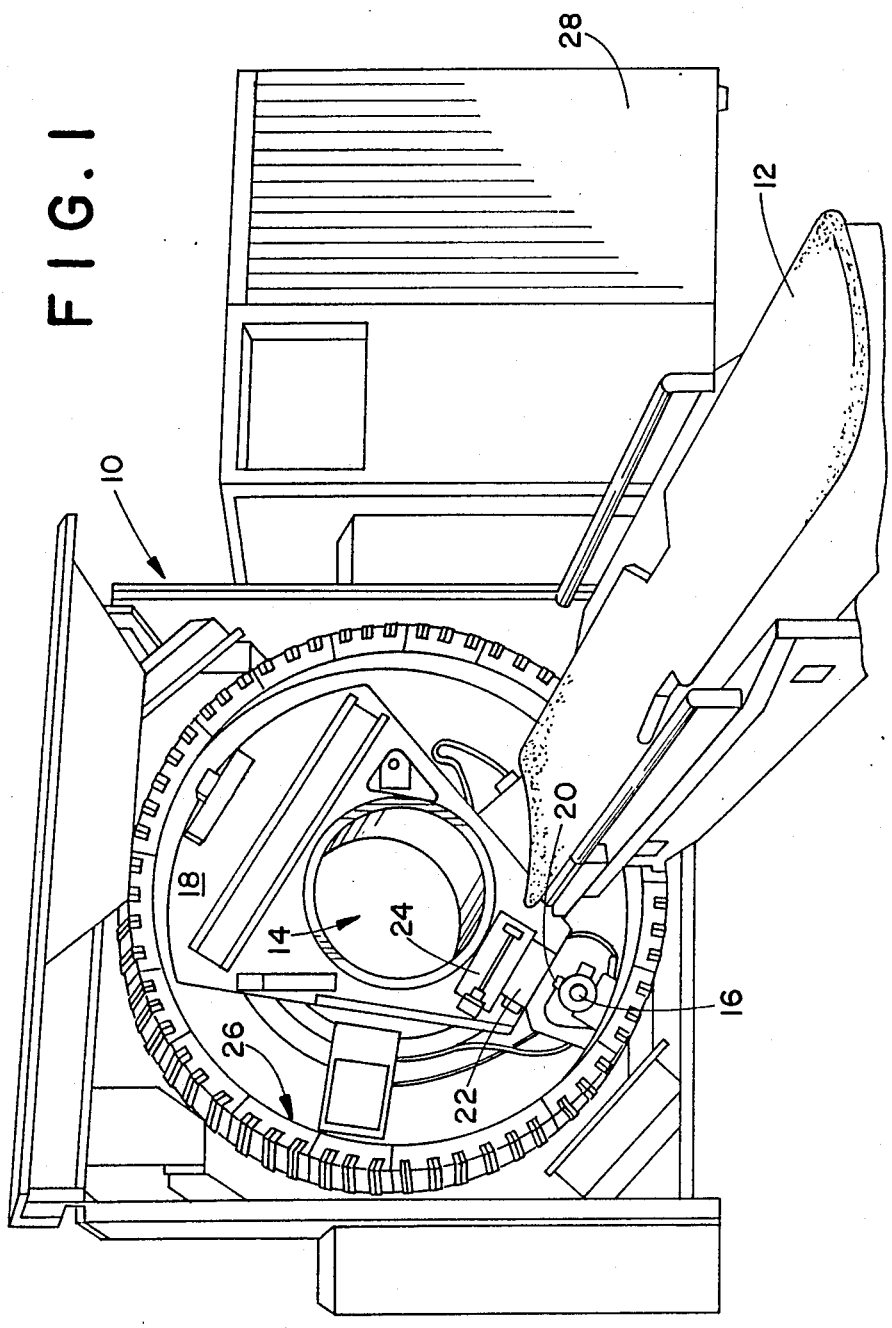
FIG. 1 is a diagrammatic illustration of a computed tomography scanner in accordance with the present invention.

With reference to FIG. 1, a computed tomography scanner 10 selectively images cross sectional slices of a region of a patient supported on a patient couch 12 within a scan circle or patient aperture 14. An x-ray tube 16 for emitting a fan shaped beam of radiation toward and spanning the scan circle 14 is mounted to a rotatable gantry 18. An off-focal radiation collimator or control means 20 is mounted to a radiation port of the x-ray tube to attenuate off-focal radiation from reaching the scan circle. A shutter 22 selectively gates the x-ray beam to permit and block it from reaching the scan circle. A primary collimator 24 selectively adjusts the dimensions of the x-ray beam, particularly its width to select the thickness of the slice which is imaged. An array of radiation detectors 26 is disposed opposite the scan circle from the x-ray tube to receive and convert radiation which has traversed the scan circle into data indicative of x-ray intensity. An image reconstruction means 28 such as the high speed data processing computer reconstructs one or more image representations from the intensity data.

In operation, a patient disposed on the patient supporting couch 12 is moved into the patient receiving region until the region of interest is appropriately positioned in the scan circle. The shutter 22 allows the fan shaped beam of radiation from the x-ray tube to traverse the scan circle 14 as an electrical motor (not shown) commences rotating the gantry 18. As the gantry rotates, the radiation detectors 26 each receive radiation along a series of paths. The computer 28 reconstructs a two dimensional image representation of the examined patient slice from the sampled x-ray detector radiation intensity data, data indicative of the position of the x-ray source, and the like.

With reference to FIG. 2, the x-ray tube 16 includes an anode 30 which is rotatably mounted within an evacuated glass envelope 32. A high potential difference accelerates a beam of electrons from a cathode (not shown) to the rotating anode 30. The cathode and other tube structure act to focus the beam of electrons to a rectangular or linear region (or other preselected shape) to form a focal spot 34. The anode is typically made of tungsten or similar metal with a high melting point. The deceleration of electrons as they strike the anode produces poly-energetic x-radiation. The radiation produced is multi-directional but generally propagates a beam toward an x-ray port 36 due to the inclined face of the anode. Scattered electrons and radiation of a commensurate energy strike the anode at regions displaced from the focal spot causing the off-focal radiation to be emitted.

A metal housing 40 surrounds the glass envelope 32 to define an oil receiving reservoir 42 therebetween. Oil from within the reservoir is commonly circulated to a cooling system (not shown) to control the temperature of the x-ray tube. The x-ray port 36 is defined by an aperture 44 in the housing which is sealed by a fluid impermeable, x-ray transmissive window 46, e.g. an aluminum sheet. The housing includes a collar 48 which surrounds the x-ray port 36 for greater structural strength.

With continuing reference to FIG. 2 and particular reference to FIGS. 3 and 4, the adjustable, off-focal collimator or control means 20 is mounted within the collar 48 which surrounds the x-ray port 36. The aluminum window 46 is mounted at an inner or near end of the collar and a first stationary, radiation or blocking plate or member 50 is mounted stationarily to a distal end of the collar. The first, stationary plate 50 is constructed of a dense x-ray absorbing material or materials. For example, the plate may include one or more layers of lead supported on a structurally stronger material which may also have high energy absorbing properties. The first stationary plate 50 includes an x-ray passing region 52, such as an elongated slot. The length and width of the x-ray passing region limit the span and thickness of the x-ray beam and to a limited extent block off-focal radiation from reaching the radiation sensors 26.

A second moveable radiation attentuation or blocking member or plate 60 is moveably mounted in the collar. The second, moveable plate is again constructed of a dense x-ray absorbing material, such as tungsten, tantalum, or reinforced lead alloys. The second, moveable plate defines at least a first or whole body scan radiation passing portion 62 and a second or head scan radiation passing portion 64. The second, moveable plate is mounted as close to the focal spot 34 as the aluminum window 46 permits. The closer the second, moveable plate is mounted to the focal spot, the more completely it blocks off-focal radiation. In the preferred embodiment, the first radiation passing portion is a slot or aperture portion which permits the beam to have a fan angle of about 41°, sufficient to span the scan circle 14 for whole body imaging. The second radiation passing portion is a shorter slot or aperture portion which limits the fan to a span of about 25½° for head scans. The shorter slot blocks the radiation which is unused in reconstructing a head image from reaching the patient receiving area to reduce scattered radiation and the potential x-ray dose which the patient might receive.

The moveable plate 60 is mounted by a bearing 70 or other moveable mounting means to a stationary supporting structure 72 which is affixed to the collar 48. The bearing enables the moveable plate to rotate about a central beam axis 74 at which the first and second energy passing portions cross. A first stop pin arrangement 76a, 76b limits rotational movement of the plate in one direction to a first position in which the first radiation passing portion 62 is aligned with the stationary radiation passing region 52. A second pin arrangement 78a, 78b, limits rotation of the moveable plate in the other direction to a second position in which the second radiation passing portion 64 is aligned with the stationary radiation passing region 52.

A plate moving or rotating means 80 includes an electrical motor 82 which selectively retracts a cable 84. Retraction of the cable is limited by the second set of interacting stop pins 78a, 78b. A spring 86 returns the moveable plate to the first position. In this manner, the spring provides a return to the first position whenever power is terminated.

With reference again to FIG. 2 and further reference to FIG. 5, the fan beam of radiation from the off-focal collimator 20 is gated by the shutter 22 to the collimator 24. The primary collimator assembly 24 includes a pair of radiation absorbing vanes 90 which lie in a common plane parallel to the path of the x-ray beam. Vane mounting means 92 movably support the vanes such that the vanes are moveable toward and away from each other. The vane mounting structure includes end plates 94 of a radiation absorbing material which define the overall width of the x-ray fan beam. As is conventional, the spacing of the end plates 94 is selected such that the fan beam of radiation spans the scan circle. A collimator adjustment motor 96 provides the motive power to adjust the width defined between the collimator vanes 90.

The invention has been described with reference to the preferred embodiments. Obviously, modifications and alterations will occur to others upon reading and understanding the preceding detailed description. It is intended that the invention be construed as including all such alterations and modifications insofar as they come within the scope of the appended claims or the equivalents thereof.

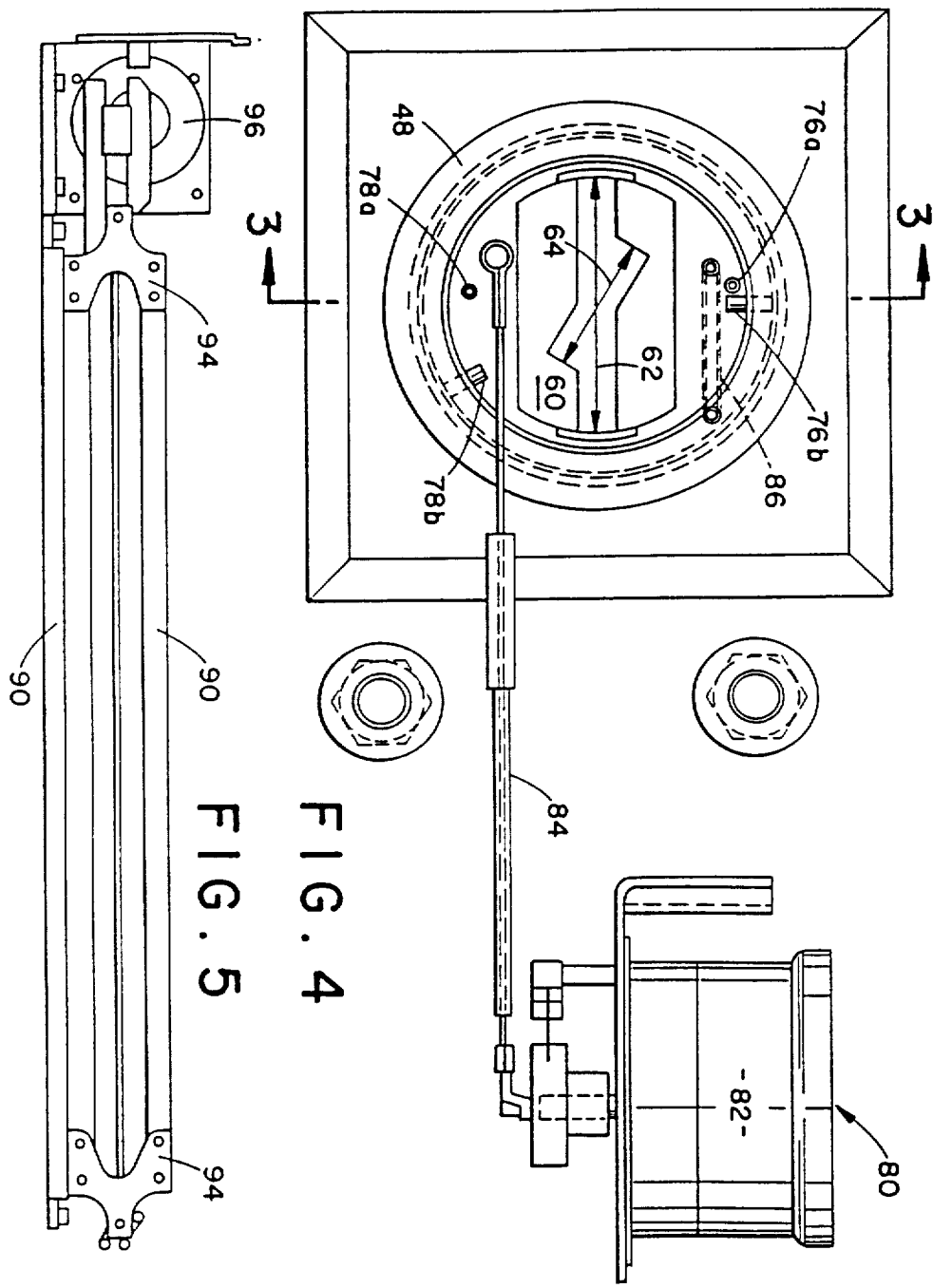

Having thus described the preferred embodiments, the invention is now claimed to be:

1. An x-ray tube assembly for radiographic scanners, the tube assembly comprising:
    an evacuated envelope;
    an anode rotatably mounted within the envelope;
    a housing surrounding the envelope to define a cooling fluid reservoir therebetween, the housing defining an aperture therein and having a collar surrounding the aperture;
    an x-ray permeable, fluid impermeable window mounted to the housing to seal the aperture;
    an x-ray beam defining means including a first radiation attenuating member with a first radiation passing region therein, the first member being mounted with the collar;
    an off-focal radiation attenuating means including a moveable second radiation attenuating member, movably mounted in relation to the first radiation attenuating member, which defines first and second radiation passing portions, the second member being movably mounted to the collar to be moveable at least between a first position in which the first radiation passing portion is aligned with the radiation passing region and a second position in which the second radiation passing portion is aligned with the radiation passing region;
    a flexible cable means interconnected between the moveable second member and a source of motive power for moving the moveable second member at least between the first and second positions;
    a first stop means for preventing rotation of the moveable second member past the first position and a second stop means for preventing rotation of the moveable second member in an opposite direction past the second position.

2. The x-ray tube assembly as set forth in claim 1 further including a spring means operatively connected with the moveable second member for biasing the moveable second member to rotate toward the first position.

3. The x-ray tube assembly as set forth in claim 1 wherein:
    the window is an aluminum sheet disposed perpendicular to a central beam axis and closely adjacent the rotatably mounted anode;
    the second moveable radiation blocking member is mounted closely adjacent the aluminum window; and,
    the first radiation attenuating member is stationary mounted adjacent a distal end of the collar of the window.

4. A radiographic scanner comprising:
    a source of penetrating radiation for projecting a generally fan shaped beam of radiation;
    an off-focal radiation absorbing plate defining first and second differently dimensioned radiation passing portions which cross at the axis of rotation;
    a moveable mounting means for movably mounting the off-focal radiation absorbing plate adjacent the radiation source such that each of the radiation passing portions is selectively moveably into alignment with the radiation beam, the moveable mounting means mounting the off-focal radiation absorbing plate for rotation about an axis which is generally parallel to a central axis of the radiation beam;
    a shutter means disposed between the off-focal radiation absorbing plate and a patient receiving region for selectively gating the radiation beam therepast to irradiate a selected region of the patient;
    a beam collimating means disposed between the off-focal radiation absorbing plate and the patient receiving region for collimating the radiation beam; and,
    a radiation detecting means for receiving radiation from the radiation source which has traversed the patient.

5. A radiographic scanner comprising:
    a source of penetrating radiation for projecting a generally fan shaped beam of radiation;
    an off-focal radiation absorbing means including a radiation attenuating member which has at least first and second differently dimensioned radiation passing portions;
    a moveable mounting means for movably mounting the radiation attenuating member adjacent the radiation source for rotation about an axis which is generally parallel to a central axis of the radiation beam such that one of the radiation passing portions is selectively moveable into alignment with the radiation beam;
    a shutter means disposed between the moveable radiation attenuating member and a patient receiving region for selectively gating the radiation beam therepast to irradiate a selected region of the patient;
    a beam collimating means disposed between the moveable radiation attenuating member and the patient receiving region for collimating the radiation beam;
    radiation detecting means for receiving radiation from the radiation source which has traversed the patient;
    a stationary radiation absorbing member mounted adjacent the moveable radiation attenuating member and having a radiation passing slot therein for passing the radiation therethrough, the first radiation passing portion of the moveable radiation attenuating member being aligned with the stationary slot in a first position and the second radiation passing portion being aligned with the stationary slot in a second position; and
a flexible cable interconnecting the moveable radiation attenuating member with a source of motive power for selectively moving the moveable radiation attenuating member between the first and second positions.

6. An x-ray tube assembly for radiographic scanners, the tube assembly comprising:
an evacuated envelope;
an anode rotatably mounted within the envelope;
a housing surrounding the envelope to define a cooling fluid reservoir therebetween, the housing defining an aperture therein and having a collar mounted thereto surrounding the aperture;
an x-ray permeable, fluid impermeable window mounted to the housing extending into and sealing the housing aperture;
an x-ray beam defining means including a first radiation attenuating member with a first radiation passing region therein, the first member being mounted within the collar extending within the housing aperture immediately contiguous to the window;
an off-focal radiation attenuating means including a second radiation attenuating member which defines first and second radiation passing portions, the second member being moveably mounted within the collar and extending within the housing aperture immediately contiguous to the beam defining means for movement at least between a first position in which the first radiation passing portion is aligned with the radiation passing region and a second position in which the second radiation passing portion is aligned with the radiation passing region, such that the off-focal radiation attenuating means is disposed as close to the anode as the window permits; and,
means for moving the second member at least between the first and second positions.

7. The x-ray tube assembly as set forth in claim 6 further including a bearing means for mounting the moveable, second member within the collar for rotation about an axis generally parallel to a defined radiation beam.

8. The x-ray tube assembly as set forth in claim 6 further including a first stop means for preventing rotation of the moveable second member past the first position and a second stop means for preventing rotation of the moveable second member in an opposite direction past the second position.

9. A radiographic apparatus comprising:
an evacuated x-ray tube envelope;
an anode disposed in the envelope for emitting radiation from a focal spot thereon, off-focal radiation being emitted from areas of the anode adjacent the focal spot;
a housing surrounding the envelope;
an aperture defined in the housing adjacent the focal spot and closed by an x-ray permeable window such that a beam of emitted x-rays pass therethrough;
a near end plate mounted inside the housing aperture immediately contiguous to the window, the near end plate being constructed of a radiation attenuating material and defining an elongated radiation passing portion therethrough;
a distal end plate of radiation attenuating material mounted inside the housing aperture contiguous to the window opposite the near end plate from the focal spot and defining an elongated x-ray passing region;
a means for moving at least one of the near and distal plates for selectively moving the radiation passing region and portion thereof selectively into and out of alignment; and,
a patient supporting means for supporting a portion of a patient to be irradiated generally in alignment with the focal spot and the near and distal plates.

10. The apparatus as set forth in claim 9 wherein the moveably mounted plate is mounted for rotation about an axis extending between the focal spot and the patient supporting means.

11. The apparatus as set forth in claim 9 wherein the near end plate includes two radiation passing portions, each of different dimension and the near end plate moveably mounted such that each of the radiation passing portions is selectively moveable into alignment with the distal end plate radiation passing portion.

12. A radiographic apparatus comprising:
an evacuated x-ray tube envelope;
an anode disposed in the envelope for emitting radiation from a focal spot thereon, off-focal radiation being emitted from areas of the anode adjacent the focal spot;
an x-ray port mounted adjacent the envelope and the focal spot such that a beam of emitted x-rays pass therethrough;
a near end plate constructed of a radiation attenuating material and defining a plurality of crossed elongated radiation passing portions that cross at an axis extending between the focal spot and a patient support means;
a means for mounting the near end plate for rotation around the axis extending between the focal spot and the patient support means;
a distal end plate of radiation attenuating material disposed opposite the near end plate from the focal spot and defining an elongated x-ray passing region; and,
a means for moving at least one of the near and distal plates for selectively moving the elongated radiation passing region of the distal end plate and each of the elongated radiation passing portions of the near end plate selectively into and out of alignment.

13. A method of radiography comprising:
rotatably mounting a generally planar radiation blocking member which has at least a larger radiation passing portion and a smaller radiation passing portion recessed inside an aperture in a housing of an x-ray tube immediately contiguous of a radiation passing window;
mounting the x-ray tube within a radiographic apparatus for irradiating a patient with radiation emitted through the x-ray tube port along a central axis;
positioning a larger portion of a patient within the radiographic apparatus in alignment with the x-ray port, moving the radiation blocking member within a plane perpendicular to the emitted radiation until the larger dimension radiation passing portion is in alignment with the patient, and irradiating the aligned larger patient portion with x-rays from the x-ray tube port;
disposing a smaller portion of a patient in the radiographic apparatus in alignment with the x-ray port, moving the radiation blocking member within the perpendicular plane until the smaller dimension x-ray passing portion is in alignment with the portion of the patient to be irradiated, and irradiating the patient with x-rays from the x-ray tube port.

* * * * *

UNITED STATES PATENT AND TRADEMARK OFFICE
CERTIFICATE OF CORRECTION

PATENT NO. : 4,905,268
DATED : February 27, 1990
INVENTOR(S) : Rodney A. Mattson, et. al.

It is certified that error appears in the above-indentified patent and that said Letters Patent is hereby corrected as shown below:

The drawing sheet, consisting of Figs. 4 and 5 should be added as shown on the attached sheet.

Signed and Sealed this

Seventh Day of June, 1994

Attest:

BRUCE LEHMAN

Attesting Officer         Commissioner of Patents and Trademarks